US012766219B2

(12) United States Patent
Robinson et al.

(10) Patent No.: US 12,766,219 B2
(45) Date of Patent: Oct. 20, 2026

(54) BIO-ABSORBABLE DISPERSIBLE RAPIDLY DEPLOYABLE WOUND INTERFACE

(71) Applicant: KCI Manufacturing Unlimited Company, Westmeath (IE)

(72) Inventors: Timothy Mark Robinson, San Antonio, TX (US); Christopher Brian Locke, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 421 days.

(21) Appl. No.: 18/287,149

(22) PCT Filed: May 3, 2022

(86) PCT No.: PCT/IB2022/054067

§ 371 (c)(1),
(2) Date: Oct. 16, 2023

(87) PCT Pub. No.: WO2022/234444

PCT Pub. Date: Nov. 10, 2022

(65) Prior Publication Data

US 2024/0408272 A1 Dec. 12, 2024

Related U.S. Application Data

(60) Provisional application No. 63/185,139, filed on May 6, 2021.

(51) Int. Cl.
*A61L 27/56* (2006.01)
*A61L 27/20* (2006.01)
*A61L 27/58* (2006.01)

(52) U.S. Cl.
CPC .............. *A61L 27/20* (2013.01); *A61L 27/56* (2013.01); *A61L 27/58* (2013.01); *A61L 2400/06* (2013.01)

(58) Field of Classification Search
CPC ... A61B 17/00491; A61M 3/00; A61M 11/02; A61M 11/00; A61M 35/003; A61M 15/0003; A61M 15/155
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Cuadros, T., et al., Carbohydrate Polymers 89: 1198 â 1206 (2012). (Year: 2012).*
(Continued)

*Primary Examiner* — Laura A Bouchelle

(57) ABSTRACT

The present disclosure provides multivalent cation alginate (e.g., calcium alginate) string wound filler compositions suitable for negative pressure wound therapy. In particular, wound filler compositions are well-suited to filling in complex wound sites, retain porosity when compressed under negative pressure, and resorbable/dispersible if left in contact with the wound beyond 7 days.

6 Claims, 11 Drawing Sheets

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,663,596 | B2 * | 12/2003 | Griego .............. A61M 25/0026 604/164.01 |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Eagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2014/0163491 | A1 | 6/2014 | Schuessler et al. |
| 2015/0080788 | A1 | 3/2015 | Blott et al. |
| 2016/0317356 | A1 | 11/2016 | Corley |
| 2018/0228705 | A1 | 8/2018 | Grotheer et al. |
| 2020/0188180 | A1 * | 6/2020 | Akbari ................ A61F 13/0213 |
| 2021/0252476 | A1 * | 8/2021 | Carus ...................... A61L 15/28 |

FOREIGN PATENT DOCUMENTS

| | | | |
|---|---|---|---|
| AU | 755496 | B2 | 12/2002 |
| CA | 2005436 | A1 | 6/1990 |
| DE | 2640413 | A1 | 3/1978 |
| DE | 4306478 | A1 | 9/1994 |
| DE | 29504378 | U1 | 9/1995 |
| EP | 0100148 | A1 | 2/1984 |
| EP | 117632 | A2 | 9/1984 |
| EP | 161865 | A2 | 11/1985 |
| EP | 358302 | A2 | 3/1990 |
| EP | 1018967 | A1 | 7/2000 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |

(56) References Cited

FOREIGN PATENT DOCUMENTS

| | | | |
|---|---|---|---|
| WO | 9605873 | A1 | 2/1996 |
| WO | 9718007 | A1 | 5/1997 |
| WO | 9913793 | A1 | 3/1999 |
| WO | 2005091884 | A2 | 10/2005 |
| WO | 2006005939 | A1 | 1/2006 |
| WO | 2009140376 | A1 | 11/2009 |
| WO | 2012001371 | A1 | 1/2012 |

OTHER PUBLICATIONS

Yuan, Z., et al., J. Mater. Res. 29(12): 1317 â 1325 (2014). (Year: 2014).*

PCT International Search Report/Written Opinion for PCT International Application No. PCT/IB2022/054067, mailed Aug. 16, 2022.

Kim Myoung Hwan et al: "Assessment of coaxial printability for extrusion-based bioprinting of alginate-based tubular constructs", Bioprinting, vol. 20, Dec. 1, 2020 (Dec. 1, 2020), p. e00092, XP055947235, ISSN: 2405-8866, DOI: 10.1016/j.bprint.2020.e00092. Retrieved from the Internet: URL:http://dx.doi.org/10.1016/j.bprint.2020.e00092.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Japanese Notice of Rejection for corresponding application 2023-567173, dated Apr. 28, 2026.
Myoung Hwan Kim et al., "Assessment of coaxial printability for extrusion--based bioprinting of alginate-based tubular constructs", Bioprinting, 2020, vol. 20.

* cited by examiner

BIO-ABSORBABLE DISPERSIBLE RAPIDLY DEPLOYABLE WOUND INTERFACE

CROSS-REFERENCE TO RELATED APPLICATIONS

This application claims the benefit of priority to U.S. Provisional Application No. 63/185,139, filed on May 6, 2021, which is incorporated herein by reference in its entirety.

TECHNICAL FIELD

The present technology relates generally to wound filler compositions suitable for negative pressure wound therapy.

BACKGROUND

The following description of the background of the present technology is provided simply as an aid in understanding the present technology and is not admitted to describe or constitute prior art to the present technology.

Negative pressure wound therapy (NPWT) is a type of wound therapy that involves applying negative pressure to a wound site to promote wound healing. Clinical studies have shown that providing reduced pressure in proximity to a wound site can assist in wound healing by promoting blood flow to the wound, stimulating the formation of granulation tissue, and encouraging the migration of healthy tissue over the wound. NPWT involves placement of a porous, foam interface into the wound and a semi-occlusive dressing that overlays the interface and seals the wound. However, it is still necessary to open wounds and remove and replace wound dressings within the deep wounds following NPWT, which in turn increases the risk of further wound trauma and/or infection.

There is a need for bioresorbable wound filler compositions that are suitable for negative pressure wound therapy, particularly with respect to treating deep and complex wound sites.

SUMMARY OF THE PRESENT TECHNOLOGY

In one aspect, the present disclosure provides a wound filler composition comprising a multivalent cation alginate string, wherein the multivalent cation alginate string (a) has a diameter of 1-4 mm, (b) has a durometer equivalent to about 20-70 shore and (c) is configured to be deployed into a wound to form a porous mesh. In some embodiments, the porous mesh is bioresorbed or dispersed from about 14 days after being deployed into the wound. The wound filler composition may be dispensed from a spray applicator, a static mixer, a dual syringe, or a trigger applicator. Additionally or alternatively, in some embodiments, the multivalent cation alginate string is bioresorbable and remains porous when compressed under negative pressure.

Additionally or alternatively, in some embodiments, the multivalent cation alginate string is generated by mixing sodium alginate or potassium alginate with a multivalent cation salt to form an alginate mixture. The multivalent cation salt may be a calcium salt, an iron salt (e.g., $Fe^{2+}$, $Fe^{3+}$), an aluminum salt, a zinc salt, a strontium salt, a magnesium salt, or barium salt. In certain embodiments, the multivalent cation salt is a calcium salt. In some embodiments, the sodium alginate or potassium alginate comprises 50%-80% guluronate and 50%-20% mannuronate. Additionally or alternatively, in some embodiments, the sodium alginate or potassium alginate is mixed with the calcium salt in a 10:1 ratio.

In any of the preceding embodiments of the wound filler compositions disclosed herein, the alginate mixture further comprises diatomaceous earth, cellulose fibres, polymeric fibres, polylactic acid (PLA), and polycaprolactone. In certain embodiments, the alginate mixture is cross-linked with covalently bonding additives such as catechol boronic acid or through amidation with multi-amine functional groups. In other embodiments, the alginate mixture is cross-linked with photoacids.

Additionally or alternatively, in some embodiments, the alginate mixture comprises an antimicrobial agent. Additionally or alternatively, in some embodiments, the antimicrobial agent is citric acid, formic acid, propionic acid, ascorbic acid, tartaric acid, sorbic acid, benzoic acid, fumaric acid, caprylic acid, or caproic acid. Additionally or alternatively, in certain embodiments, the antimicrobial agent includes one or more of tetracycline, penicillins, terramycins, erythromycin, bacitracin, neomycin, polymycin B, mupirocin, clindamycin, colloidal silver, silver sulfadiazine, chlorhexidine, povidone iodine, triclosan, sucralfate, quaternary ammonium salts, pharmaceutically acceptable silver salts, or any combination thereof.

Additionally or alternatively, in some embodiments, the multivalent cation alginate string comprises an outer layer of sodium or potassium alginate and an inner layer of the multivalent cation salt, or an inner layer of sodium or potassium alginate and an outer layer of the multivalent cation salt. In some embodiments, the inner layer has a width of about 0.1 mm to about 2 mm. Additionally or alternatively, in some embodiments, the outer layer has a width of about 0.1 mm to about 2 mm.

In one aspect, the present disclosure provides a canister comprising a first compartment, a second compartment, and a gas cartridge comprising a pressuring gas, wherein the first compartment includes sodium alginate or potassium alginate and the second compartment includes a multivalent cation salt, and wherein the canister is configured to dispense a multivalent cation alginate string having a durometer equivalent to about 20-70 shore and a diameter of 1-4 mm. The sodium alginate or potassium alginate may be in the form of an aqueous paste or dry powder. In some embodiments, the pressuring gas is carbon dioxide ($CO_2$).

Additionally or alternatively, in some embodiments, the canister further comprises a mixer nozzle that is configured to (a) receive the sodium alginate or potassium alginate from the first compartment and the multivalent cation salt from the second compartment and (b) mix the sodium alginate or potassium alginate with the multivalent cation salt to form an alginate mixture. In some embodiments, the multivalent cation alginate string includes an inner layer of sodium or potassium alginate and an outer layer of the multivalent cation salt, or an outer layer of sodium or potassium alginate and an inner layer of the multivalent cation salt.

In one aspect, the present disclosure provides a method for treating a wound in a subject in need thereof, comprising (a) administering any and all embodiments of the wound filler composition to a wound, wherein the wound filler composition is configured to fill an entire volume of the wound; (b) providing a device to the wound, wherein the device comprises: a drape, optionally a retainer layer, and a vacuum source for applying negative pressure to the wound, wherein the vacuum source is configured to be fluidly connected to the drape through tubing; (c) optionally applying the retainer layer over the wound filler composition; (d)

applying the drape over the wound filler composition and/or the retainer layer, wherein the drape is configured to seal the wound filler composition and/or the retainer layer and the wound; and (e) applying negative pressure to the wound.

In another aspect, the present disclosure provides a method for treating a wound in a subject in need thereof, comprising (a) administering any and all embodiments of the wound filler composition to a wound, wherein the wound filler composition is configured to fill an entire volume of the wound; (b) providing a device to the wound, wherein the device comprises: a drape, optionally a retainer layer, an instillation pump configured to instill a wound instillation fluid composition to the wound filler composition, and a vacuum source for applying negative pressure to the wound, wherein each of the vacuum source and the instillation pump are fluidly connected to the drape through tubing; (c) optionally applying the retainer layer over the wound filler composition; (d) applying the drape over the wound filler composition and/or the retainer layer, wherein the drape is configured to seal the wound filler composition and/or the retainer layer and the wound; (e) instilling the wound instillation fluid composition to the wound filler composition; (f) soaking the wound in the wound instillation fluid composition for a first temporal interval; (g) applying negative pressure on the wound for a second temporal interval; and (h) repeating steps (e)-(g) at least once. In certain embodiments, steps (e)-(g) are repeated for about 2 to about 1000 cycles. Additionally or alternatively, in some embodiments, the tubing comprises polyvinyl chloride, polyethylene, polypropylene, or any combination thereof. In yet another aspect, the present disclosure provides a method for treating a wound in a subject in need thereof, comprising (a) administering any and all embodiments of the wound filler composition of the present technology to a wound, wherein the wound filler composition is configured to fill an entire volume of the wound; (b) providing an instillation pump configured to instill a wound instillation fluid composition to the wound filler composition, and a vacuum source for applying negative pressure to the wound, wherein the vacuum source is fluidly connected to the wound filler composition through a first tube connection and the instillation pump is fluidly connected to the wound filler composition through a second tube connection; (c) instilling the wound instillation fluid composition to the wound filler composition; (d) soaking the wound in the wound instillation fluid composition for a first temporal interval; (e) applying negative pressure on the wound for a second temporal interval; and (f) repeating steps (c)-(e) at least once. In certain embodiments, steps (c)-(e) are repeated for about 2 to about 1000 cycles. Additionally or alternatively, in some embodiments, the first tube connection and/or the second connection is composed of polyvinyl chloride, polyethylene, polypropylene, or any combination thereof. In any of the preceding embodiments of the methods disclosed herein, the wound instillation fluid comprises saline solution. In some embodiments, the first temporal interval is about 10 seconds to about 30 minutes. Additionally or alternatively, in some embodiments, the second temporal interval is about 10 seconds to about 100 minutes. Additionally or alternatively, in some embodiments, the volume of the wound instillation fluid composition instilled to the wound dressing is about 1 ml to about 20 ml per cycle.

In any and all embodiments of the methods disclosed herein, the wound is a chronic wound, an acute wound, a deep wound, a partial thickness wound, a traumatic wound, a subacute wound, a dehisced wound, a partial-thickness burn, an ulcer, a flap, or a graft. The chronic wound may be selected from the group consisting of infectious wounds, venous ulcers, arterial ulcers, decubitus ulcers and diabetic ulcers. Additionally or alternatively, in some embodiments of the methods disclosed herein, the negative pressure applied to the wound filler composition is about −5 mm Hg to about −500 mm Hg, or about −75 mm Hg to about −300 mm Hg.

DETAILED DESCRIPTION

Figure 1:
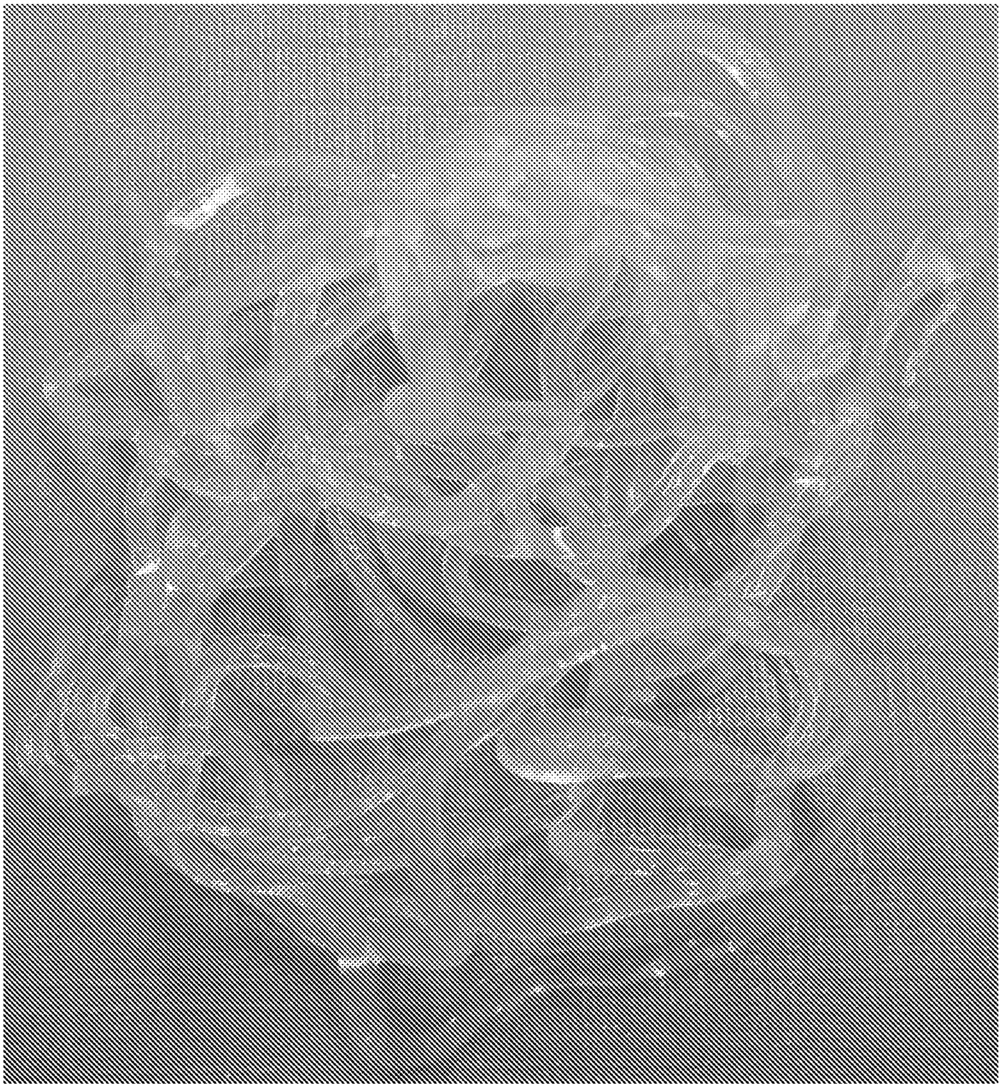
FIG. 1 shows a representative image of a calcium alginate string formed as it emerges from the nozzle of an aerosol type dispenser comprising sodium alginate in the form of an aqueous paste and a calcium salt.

It is to be appreciated that certain aspects, modes, embodiments, variations and features of the present methods are described below in various levels of detail in order to provide a substantial understanding of the present technology. It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

Existing low viscosity alginates are regarded as being too fragile of a material for use as a wound filler in negative pressure wound therapy (www.activheal.com/alginate-dressings-wound-management/) because calcium alginate gels are usually too soft and tend to break down to easily. Vassallo et al., *Wounds* Volume 27(7): 180-190 (2015); www.elenaconde.com/en/why-do-we-use-so-many-alginate-fibre-sheets-in-our-wound-clinic/). This is exacerbated by the fact that many wound fillers in negative pressure wound therapy are not resorbable, making it necessary to reopen wounds to remove and replace wound dressings following NPWT. Vassallo et al., *Wounds* Volume 27(7): 180-190 (2015); Anesäter E et al., *Int Wound J* 8(4):336-42 (2011); www.smith-nephew.com/global/assets/pdf/products/2-sn7820b-npwt-clinical_guidelines.pdf, www.acelity.com/-/media/Project/Acelity/Acelity-Base-Sites/shared/PDF/2-b-128h-vac-clinical-guidelines-web.pdf/.

The present disclosure generally provides a wound filler composition comprising an extruded multivalent cation alginate (e.g., calcium alginate) string or ribbon that can be rapidly deployed into a complex wound to form a porous mesh and possesses manifolding properties that make it suitable for NPWT. The wound filler composition of the present technology has a durometer equivalent of about 20-70 shore, allowing it to be compressible as a mass while simultaneously retaining porosity when compressed under negative pressure. The wound filler composition of the present technology is also resorbable/dispersible if left in contact with the wound beyond at least 7 days. Without wishing to be bound by theory, it is believed that long term exposure to saline solutions during negative pressure and instillation wound therapy (NPIWT) reverses calcium alginate ionic cross-links, thereby forming water soluble sodium alginate. Accordingly, the wound filler composition of the present technology can be effectively removed by applying a NaCl solution through extended instillation events, thus precluding the need to reopen complex wounds for the purpose of replacing wound dressings following NPWT. Thus, the unexpected properties of the alginate-based wound fillers of the present disclosure render them well-suited for NPWT, and thus represent a significant advance over conventional low viscosity alginates.

Definitions

Unless defined otherwise, all technical and scientific terms used herein generally have the same meaning as commonly understood by one of ordinary skill in the art to which this technology belongs.

As used herein and in the appended claims, singular articles such as "a", "an", and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of a wound filler composition to a subject includes any route of introducing or delivering to a subject a wound filler composition to perform its intended function. Administration can be carried out by any suitable route, including but not limited to, spraying or injection. Administration includes self-administration and the administration by another.

As used herein, "Alginate" refers to a linear co-polymer with homopolymeric blocks of (1-4)-linked β-D-mannuronate (M) and its C-5 epimer α-L-guluronate (G) residues, respectively, covalently linked together in different sequences or blocks.

As used herein, "bioresorbable" refers to a material that is completely removed by the surrounding biological environment (i.e. tissue) of a subject, thus leaving no foreign material in a treated wound and avoiding a persistent inflammatory response. In contrast, a "biodegradable material" is a material that is fragmented by the biological environment and leaves degradation products behind that may cause a persistent inflammatory process within the tissue. A "bioresorbable material" is absorbed or digested by the body, within a specified degradation time dictated by the chemistry of the material and material-tissue interaction. When a bioresorbable material comes into contact with the body, it is depolymerized and disintegrated into carbon dioxide ($CO_2$) and water ($H_2O$). The material structure directly affects the degradation time and the mechanical strength of the material.

As used herein, the terms "contain", "contains", or "containing" in the context of describing the elements (especially in the context of the following claims) are to be construed as comprising or including the elements being described herein.

As used herein, the term "manifold" or "manifolding" generally includes any composition or structure providing a plurality of pathways and/or perforations configured to collect or distribute fluid and/or pressure across a tissue site while under pressure.

As used herein, the term "NPWT" refers to negative pressure wound therapy, which is a type of wound therapy that involves applying negative pressure (relative to atmospheric pressure) to a wound bed to promote wound healing. NPWT provides complete coverage of a wound, constant interstitial fluid removal, and mechanical stimulation of surrounding tissues. Typically, a dressing is sealed over a wound site and air is pumped out of the dressing to create negative pressure at the wound site. In some NPWT systems, wound exudate and other fluid is pumped out of the dressing and collected by a canister.

As used herein, the terms "subject", "patient", or "individual" can be an individual organism, a vertebrate, a mammal, or a human. In some embodiments, the subject, patient or individual is a human.

"Treating" or "treatment" as used herein covers the treatment of a wound described herein, in a subject, such as a human, and includes: (i) inhibiting a wound, i.e., arresting its development; (ii) relieving a wound, i.e., causing regression of the wound; (iii) slowing progression of the wound; and/or (iv) inhibiting, relieving, or slowing progression of one or more symptoms of the wound. In some embodiments, treatment means that the symptoms associated with the wound are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

As used herein, the term "wound" refers to cuts, incisions, abrasions, lacerations, amputations, burns induced by heat, ionizing radiation, ultraviolet radiation including sunlight, electricity, or chemical substances as well as to other forms of lesions such as ulcers, pressure sores and bedsores. In some embodiments, a "wound" refers broadly to injuries to the skin and underlying (subcutaneous) tissue initiated in different ways (e.g., pressure sores from extended bed rest and wounds induced by trauma) and with varying characteristics. Wounds may be classified into one of four grades depending on the depth of the wound. Grade I wounds are limited to the epithelium. Grade II wounds extend into the dermis. Grade III wounds extend into the subcutaneous tissue; and Grade IV (or full-thickness wounds) wounds are deeper and may involve bones exposure. In some embodiments, the wound is a "Partial thickness wound." As used herein, "Partial thickness wound" refers to wounds that encompass Grades I-III; examples of partial thickness wounds include burn wounds, pressure sores, venous stasis ulcers, and diabetic ulcers. As used herein, a "Deep wound" includes both Grade III and Grade IV wounds. The present disclosure contemplates treating all wound types, including deep wounds and chronic wounds. As used herein, "Chronic wound" refers to a wound that has not healed within 30 days.

Alginates and Wound Care

Alginate is derived from seaweed and is available in the form of alginic acid, various salts, and various ester derivatives. The solubility of the alginate salt depends on the salt with which it is coupled. Alginate salts with monovalent cations such as sodium or potassium are generally soluble in water. Alginate salts formed with divalent or trivalent cations such as calcium or zinc are generally insoluble in water. Therefore, varying the sodium/calcium ratio of mixed sodium/calcium alginate salt can affect the water solubility of alginate compositions.

Alginate is recommended for exudating wounds and helps in debridement of sloughing wounds. Alginate wound dressings that are currently used in the field of wound healing, as a packing material for cavity wounds or for treatment of burns, include, but are not limited to KALTOSTAT (Britcaire Limited), SORBSAN (Pharma-Plast Limited) and ALGOSTERIL (Johnson & Johnson). For many of these commercially available alginates, it is recommended that the alginate dressings be changed daily. See e.g., *Treating Wounds with Absorbent Alginate Dressings* (Sep. 30, 2015), advancedtissue.com/2015/09/treating-wounds-with-absorbent-alginate-dressings. Although alginates have good properties for treating cavity wounds and burns, alginate is not intrinsically bioresorbable, and tends to fragment in the wound. It is therefore necessary to rinse the wound out thoroughly with saline solution to ensure that no residual alginate fragments are left in the wound. If left in the wound, fragments of alginate often result in the formation of granulomas. See, e.g, EP0849281.

Wound Filler Compositions of the Present Technology

The wound filler compositions of the present technology comprise extruded multivalent cation alginate (e.g., calcium alginate) strings or ribbons that can be rapidly deployed into a complex wound to form a porous mesh and exhibit manifolding properties that make them suitable for NPWT.

The wound filler compositions of the present disclosure represent a significant advancement over existing wound dressings. First, deployment of the multivalent cation alginate (e.g., calcium alginate) wound filler compositions of the present technology into complex wound cavities is simple and user-friendly because the wound filler compositions can be dispensed from gas or mechanically powered dispensers such as aerosol or spray applicators, static mixers, dual syringes, or trigger applicators. Second, the wound filler compositions of the present technology are bioresorbable and thus may be left in the wound for extended time periods without safety concerns. Third, the wound filler compositions of the present technology are well-suited for treating complex wounds where dressing removal may be difficult or cause undue trauma. Fourth, the wound filler compositions of the present technology may be deployed into tunneled areas of wound cavities that are difficult to reach using a nozzle. Fifth, the wound filler compositions may provide scaffold structures for in-growth or new tissues for large deep structures. Sixth, the wound filler compositions of the present technology are not soft or prone to immediate break-down like wound care alginate products that are currently used in the art. Rather, the wound filler compositions of the present technology have a durometer equivalent which allows the compositions to be spongy, conformable, and compressible under negative pressure. Accordingly, the wound filler compositions of the present technology exhibit manifolding properties that render them suitable for NPWT.

In one aspect, the present disclosure provides a wound filler composition comprising a multivalent cation alginate string, wherein the multivalent cation alginate string (a) has a diameter of about 1-4 mm, (b) has a durometer equivalent to about 20-70 shore and (c) is configured to be deployed into a wound to form a porous mesh. In some embodiments, the multivalent cation alginate string is a calcium alginate string, an iron salt (e.g., $Fe^{2+}$, $Fe^{3+}$), an aluminum salt, a zinc alginate string, a strontium alginate string, a magnesium alginate string, or barium alginate string. In certain embodiments, the multivalent cation alginate string is a calcium alginate string. Additionally or alternatively, in some embodiments, the multivalent cation alginate string is bioresorbable and remains porous when compressed under negative pressure. The wound filler compositions disclosed herein may be dispensed from gas or mechanically powered dispensers such as aerosol or spray applicators, static mixers, dual syringes, or trigger applicators.

Additionally or alternatively, in some embodiments, the multivalent cation alginate string has a diameter of about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, or about 4 mm, and/or has a durometer equivalent to about 20 shore, about 21 shore, about 22 shore, about 23 shore, about 24 shore, about 25 shore, about 26 shore, about 27 shore, about 28 shore, about 29 shore, about 30 shore, about 31 shore, about 32 shore, about 33 shore, about 34 shore, about 35 shore, about 36 shore, about 37 shore, about 38 shore, about 39 shore, about 40 shore, about 41 shore, about 42 shore, about 43 shore, about 44 shore, about 45 shore, about 46 shore, about 47 shore, about 48 shore, about 49 shore, about 50 shore, about 51 shore, about 52 shore, about 53 shore, about 54 shore, about 55 shore, about 56 shore, about 57 shore, about 58 shore, about 59 shore, about 60 shore, about 61 shore, about 62 shore, about 63 shore, about 64 shore, about 65 shore, about 66 shore, about 67 shore, about 68 shore, about 69 shore, or about 70 shore.

In any of the preceding embodiments, the multivalent cation alginate string is generated by mixing sodium alginate or potassium alginate with a multivalent cation salt to form an alginate mixture. The sodium or potassium alginate may have a viscosity that is low viscosity (<240 mPas), medium viscosity (240-3500 mPas), or high viscosity (>3500 mPas). In certain embodiments, the sodium or potassium alginate is a low viscosity sodium or potassium alginate having a solids content of up to 10%-25% w/w. In some embodiments, the sodium or potassium alginate is a low viscosity sodium or potassium alginate having a solids content of up to 10% w/w, up to 11% w/w, up to 12% w/w, up to 13% w/w, up to 14% w/w, up to 15% w/w, up to 16% w/w, up to 17% w/w, up to 18% w/w, up to 19% w/w, up to 20% w/w, up to 21% w/w, up to 22% w/w, up to 23% w/w, up to 24% w/w, or up to 25% w/w. The multivalent cation salt may be a calcium salt, an iron salt (e.g., $Fe^{2+}$, $Fe^{3+}$), an aluminum salt, a zinc salt, a strontium salt, a magnesium salt, or barium salt. Additionally or alternatively, the multivalent cation salt may be calcium chloride, iron chloride, aluminum chloride, zinc chloride, strontium chloride, magnesium chloride, or barium chloride. In certain embodiments, the calcium salt is 1%, 2%, 3%, 4%, 5%, 6%, 7%, 8%, 9% or 10% $CaCl_2$ solution. Additionally or alternatively, in some embodiments, the sodium alginate or potassium alginate is mixed with the calcium salt in a 10:1 ratio.

In any and all of the embodiments disclosed herein, the sodium alginate or potassium alginate comprises about 50%-80% guluronate and about 50%-20% mannuronate. In certain embodiments, the sodium alginate or potassium alginate comprises about 50% guluronate and about 50% mannuronate, about 55% guluronate and about 45% mannuronate, about 60% guluronate and about 40% mannuronate, about 65% guluronate and about 35% mannuronate, about 70% guluronate and about 30% mannuronate, about 75% guluronate and about 25% mannuronate, or about 80% guluronate and about 20% mannuronate.

Other additives may be added to the alginate mixture to modify the strength and rate of absorbency of the wound filler compositions of the present technology. Accordingly, in any of the preceding embodiments of the wound filler compositions disclosed herein, the alginate mixture further comprises diatomaceous earth, cellulose fibres, polymeric fibres, polylactic acid (PLA), and polycaprolactone. Additionally or alternatively, in certain embodiments, the alginate mixture is cross-linked with covalently bonding additives (e.g., catechols and boronic acid) or through amidation with multi-amine functional groups to provide a longer lasting and stronger wound filler. In other embodiments, the alginate mixture is cross-linked with photoacids. For example, light sensitive agents generate an acid on exposure to light (typically UV) and may directly crosslink the alginate, or act on a insoluble or partially soluble calcium salt (such as calcium carbonate) to release calcium ions. In any of the preceding embodiments of the wound filler compositions disclosed herein, a propelling gas is mixed with the sodium or potassium alginate to form a foam. In some embodiments, the propelling gas is carbon dioxide.

Additionally or alternatively, in some embodiments, the alginate mixture further comprises an antimicrobial agent. In some embodiments, the antimicrobial agent is citric acid, formic acid, propionic acid, ascorbic acid, tartaric acid, sorbic acid, benzoic acid, fumaric acid, caprylic acid, or caproic acid. Additionally or alternatively, in certain embodiments, the antimicrobial agent includes one or more of tetracycline, penicillins, terramycins, erythromycin, bacitracin, neomycin, polymycin B, mupirocin, clindamycin, colloidal silver, silver sulfadiazine, chlorhexidine, povidone iodine, triclosan, sucralfate, quaternary ammonium salts, pharmaceutically acceptable silver salts, or any combination thereof.

Additionally or alternatively, in some embodiments, the alginate mixture further comprises a wound healing agent. As used herein, a "wound healing agent" is an agent that accelerates the wound healing process. In some exemplary embodiments, a wound healing agent may be combined or used together or in coordination with an antibiotic, antifungal, or antiviral substance or substances that accelerate the healing of sores or other infection-damaged tissue simultaneously or sequentially with the treatment of the underlying infection. Examples of wound healing agents include, but are not limited to, Adrenaline, Platelets and/or platelet extracts, β-lactams, Diphenhydramine, Ribonucleosides, Penicillins, Loratadine, Proline, Cephalosporins, Meclizine, Lysine, Monobactams, Quetiapine, Elastin, Macrolides, Cromoglicate (cromolyn), Glycosaminoglycans, Polymyxins, Nedocromil, Spermidine, Tetracyclines, Caffeine, Spermine Chloramphenicol, Ephedrine, Putrescine, Thrimethoprim, Oxymetazoline, Angiogenic factors, Aminoglycosides, Phenylephrine, Zinc, Clindamycin, Pseudoephedrine, Somatomedins, Metronidazole, Tramazoline, Lamin, Sulphadimidine, Phenylpropanolamine, FGF, Sulphadimethoxin, Xylometazoline, PDGF, Amphotericin B, Corticosteroid, TGF, Ketoconazol, Allantoin, IGF, Miconazol, Retinoic acid, EGF, Idoxuridine, Aloe vera, MDGF, Azidothymidin, Glycine, NGF, Halogens, Vitamin A, KGF, Chlorohexidine, B vitamins, TNF Silver ions nicotinamide, Vitamin C PDECGF, alpha-1 antitrypsin, Vitamin E, Bacitracin, SLPI, Comfrey root preparations, Neomycin, Quaternary ammonium, Polymyxin compounds.

Additionally or alternatively, in some embodiments, the multivalent cation alginate string comprises (i) an outer layer of sodium or potassium alginate and an inner layer of the multivalent cation salt, or (ii) an inner layer of sodium or potassium alginate and an outer layer of the multivalent cation salt. In some embodiments, the inner layer has a width of about 0.1 mm to about 3.9 mm. Additionally or alternatively, in some embodiments, the outer layer has a width of about 0.1 mm to about 3.9 mm. In certain embodiments, the inner layer and/or the outer layer has a width of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, or about 3.9 mm.

In any and all embodiments of the wound filler compositions disclosed herein, the porous mesh is bioresorbed or dispersed from about 14 days after being deployed into the wound. By way of example, and without any limitation, in some embodiments, the porous mesh is bioresorbed or dispersed and shows a decrease in durometer by about 20% in about 7 days after being deployed into the wound. In certain embodiments, the porous mesh can be removed as a single mass in about 7 days after being deployed into the wound. Additionally or alternatively, in some embodiments, the porous mesh is bioresorbed or dispersed and shows a decrease in durometer by about 50% in about 10 days after being deployed into the wound. In certain embodiments, the porous mesh is completely bioresorbed or dispersed in more than 14 days after being deployed into the wound. In some embodiments, the time frame by which the porous mesh is fully reabsorbed may be changed. Accordingly, wound filling compositions with different strengths and healing periods may be produced based on wound depth, and the number of times a dressing may be changed. In some embodiments, the wound filling composition may be used as a scaffold structure for in-growth by new tissues by changing the time by which the wound filling composition is completely reabsorbed. In some embodiments, the wound filling composition is optimized to form a structure intended for in-growth by new tissues and thus serve as a scaffold structure.

Wound Care Canisters of the Present Technology

In one aspect, the present disclosure provides a canister for dispensing any and all embodiments of the wound filling compositions described herein. The wound filler compositions disclosed herein may be dispensed from gas or mechanically powered dispensers such as aerosol or spray applicators, static mixers, dual syringes, or trigger applicators. In some embodiments, the wound filler composition is dispensed from an aerosol type dispenser such as a compressed gas canister.

In some embodiments, the wound filler compositions of the present disclosure are generated by mixing sodium alginate or potassium alginate with a multivalent cation salt in a canister to form an alginate mixture. In some embodiments, the canister comprises a mixer nozzle which includes a spiral mixing section where different components are brought together. Additionally or alternatively, in some embodiments, sodium alginate or potassium alginate in the form of an aqueous paste is delivered into the mixer nozzle where it mixes together with a multivalent cation salt (e.g., a calcium salt such as $CaCl_2$) to form an alginate mixture that is configured to be extruded as a multivalent cation alginate string. In other embodiments, a multivalent cation salt (e.g., a calcium salt such as $CaCl_2$) may be mixed with sodium alginate or potassium alginate to form a dry mix in a compressed gas canister, which is then dispensed into a flow of water driven by compressed gas pressure. In one embodiment, the compressed gas is $CO_2$. Various disposable nozzles of various lengths and cross sectional shapes may be attached to the canister. Without wishing to be bound by theory, it is believed that ion exchange between the multivalent cation salt and the sodium alginate or potassium alginate occurs rapidly such that the water insoluble and cross-linked multivalent cation alginate is formed as it emerges from the nozzle of the canister (see FIG. 1).

The canister used to dispense the wound filling compositions of the present technology may comprise at least two compartments. In one aspect, the present disclosure provides a canister comprising a first compartment and a second compartment, wherein the first compartment includes sodium alginate or potassium alginate and the second compartment includes a multivalent cation salt, and wherein the canister is configured to dispense a multivalent cation alginate string having a durometer equivalent to about 20-70 shore and a diameter of 1-4 mm. In certain embodiments, the canister includes a gas cartridge comprising a pressuring gas. In some embodiments, the pressuring gas is carbon dioxide ($CO_2$). The sodium alginate or potassium alginate may be in the form of an aqueous paste or dry powder.

Additionally or alternatively, in some embodiments, the canister further comprises a mixer nozzle that is configured to (a) receive the sodium alginate or potassium alginate from the first compartment and the multivalent cation salt from the second compartment and (b) mix the sodium alginate or potassium alginate with the multivalent cation salt to form an alginate mixture. In some embodiments, the canister includes a gas cartridge and pressurizing gas from the gas cartridge is configured to dispense the multivalent cation alginate string as it emerges from the nozzle of the canister. In some embodiments, the canister is configured to extrude a multivalent cation alginate string having an inner layer of sodium or potassium alginate and an outer layer of the multivalent cation salt, or an outer layer of sodium or potassium alginate and an inner layer of the multivalent cation salt.

Figure 5:
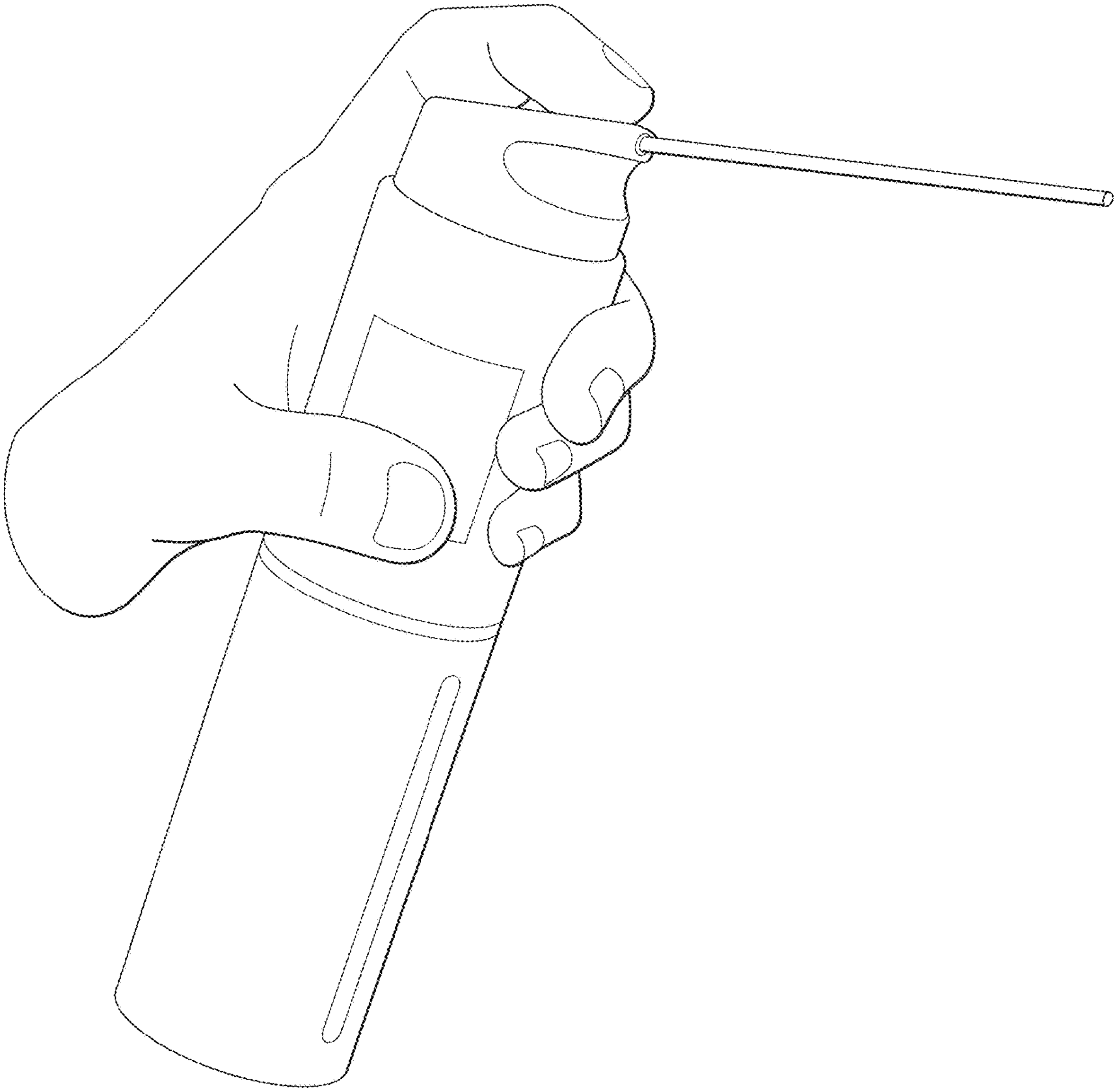
FIG. 5 shows an example of a gas powered applicator that can be used to dispense the calcium alginate wound filler of the present technology.
Figure 6:
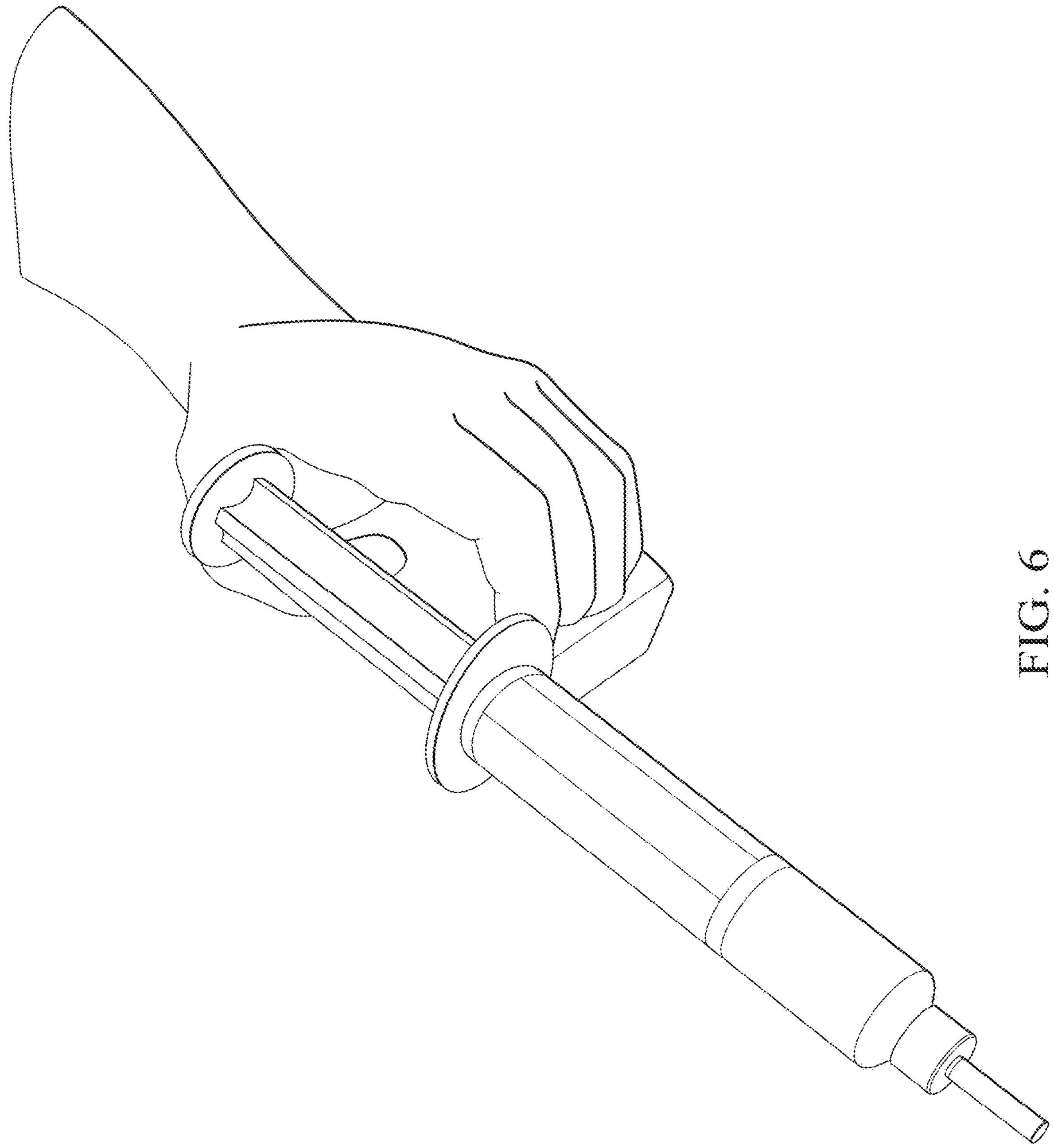
FIG. 6 shows an example of a mechanically powered applicator that can be used to dispense the calcium alginate wound filler of the present technology.

In some embodiments, the canister is a gas or mechanically powered applicator that is configured to bring together the sodium alginate or potassium alginate with a crosslinking agent (such as for example a multivalent cation salt). In some embodiments, the applicator uses static mixers in combination with a surface cure facility. In some embodiments, the surface cure provides a way to achieve a fast cure nonstick surface on the extrusion and is achieved by passing the sodium alginate or potassium alginate through a porous die or tube. In some embodiments, the porous die permits the sodium alginate or potassium alginate to come into contact with the crosslinking agent as it is extruded. Exemplary applicators contemplated by the present disclosure are shown in FIGS. 5-6. Additionally or alternatively, in some embodiments, the canister is formed from static mixer designs, wherein the sodium alginate or potassium alginate is mixed with the multivalent cation salt (e.g., calcium chloride) as a low viscosity solution. In other embodiments, the canister is formed from static mixer designs, wherein the sodium alginate or potassium alginate is mixed in with a carrier to match the viscosity of the sodium alginate or potassium alginate to improve mixing. In certain embodiments, the carrier is a water-soluble copolymer such as polyvinyl alcohol, polyvinyl pyrrolidone, or chitosan. Chitosan requires a low pH to form solutions, which may be achieved with weak acids such as acetic acid or citric acid. Furthermore, chitosan is cationic in nature and will additionally react with the anionic alginate. In some embodiments, a neutralizing salt is added to the alginate to counteract the weak acid used with the chitosan. In some embodiments, the neutralizing salt is selected from a carbonate or bicarbonate. In some embodiments, the resulting carbon dioxide formed by mixing the neutralizing salt and the acid adds bulk to the wound filler.

Additionally or alternatively, in some embodiments, the sodium alginate or potassium alginate may be cross-linked through the use of light. In certain embodiments, calcium carbonate and a photoacid are added to a soluble sodium alginate or potassium alginate, wherein the calcium carbonate provides a potential supply of calcium ions, and the mixture is exposed to light (typically UV) to release acid, wherein the acid releases the calcium ions from the carbonate and the calcium ions react with the sodium alginate or potassium alginate.

NPWT Systems

"NPWT" refers to negative pressure wound therapy, which is a type of wound therapy that involves applying negative pressure (relative to atmospheric pressure) to a wound bed to promote wound healing. Typically, a dressing is sealed over a wound site and air is pumped out of the dressing to create negative pressure at the wound site. In some NPWT systems, wound exudate and other fluid is pumped out of the dressing and collected by a canister. In any embodiment of the wound filler composition disclosed herein, the wound filler composition of the present technology is configured for use in negative pressure wound therapy (NPWT). Additionally or alternatively, in some embodiments, NPWT may be performed such as by procedures described in U.S. Pat. Nos. 7,534,240 and 9,918,733, the entire contents of which are incorporated by reference.

In any embodiment of the wound filler composition disclosed herein, the application of the wound filler composition of the present technology causes about 50% to about 100% reduction in pressure drop observed in negative pressure wound therapy compared to that observed with a control foam (e.g., granufoam). Additionally or alternatively, in some embodiments of the wound filler composition disclosed herein, the application of the wound filler composition of the present technology causes about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, about 100%, or any range including and/or in between any two of these values, reduction in the pressure drop observed in negative pressure wound therapy compared to that observed with a control foam (e.g., granufoam).

In any embodiment disclosed herein, the wound filler compositions of the present technology advantageously exhibit improved manifolding and decreased pressure drop observed in NPWT. Without wishing to be bound by theory, it is believed that the wound filler compositions of the present technology are able to impart constant pressure distribution across a wound site upon application.

Figure 7:
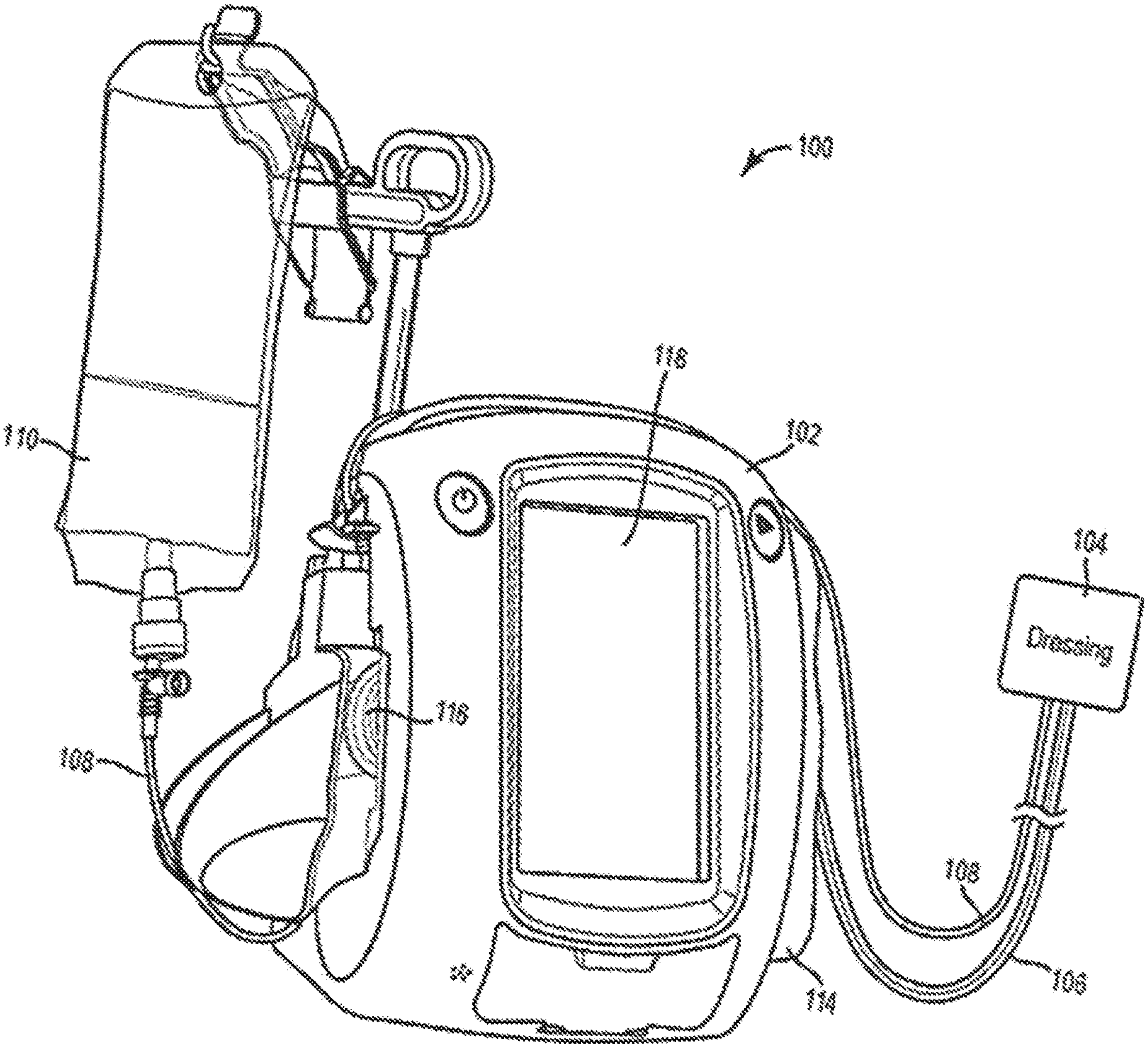
FIG. 7 is a perspective view of an exemplary negative pressure and instillation wound therapy system.
Figure 8:
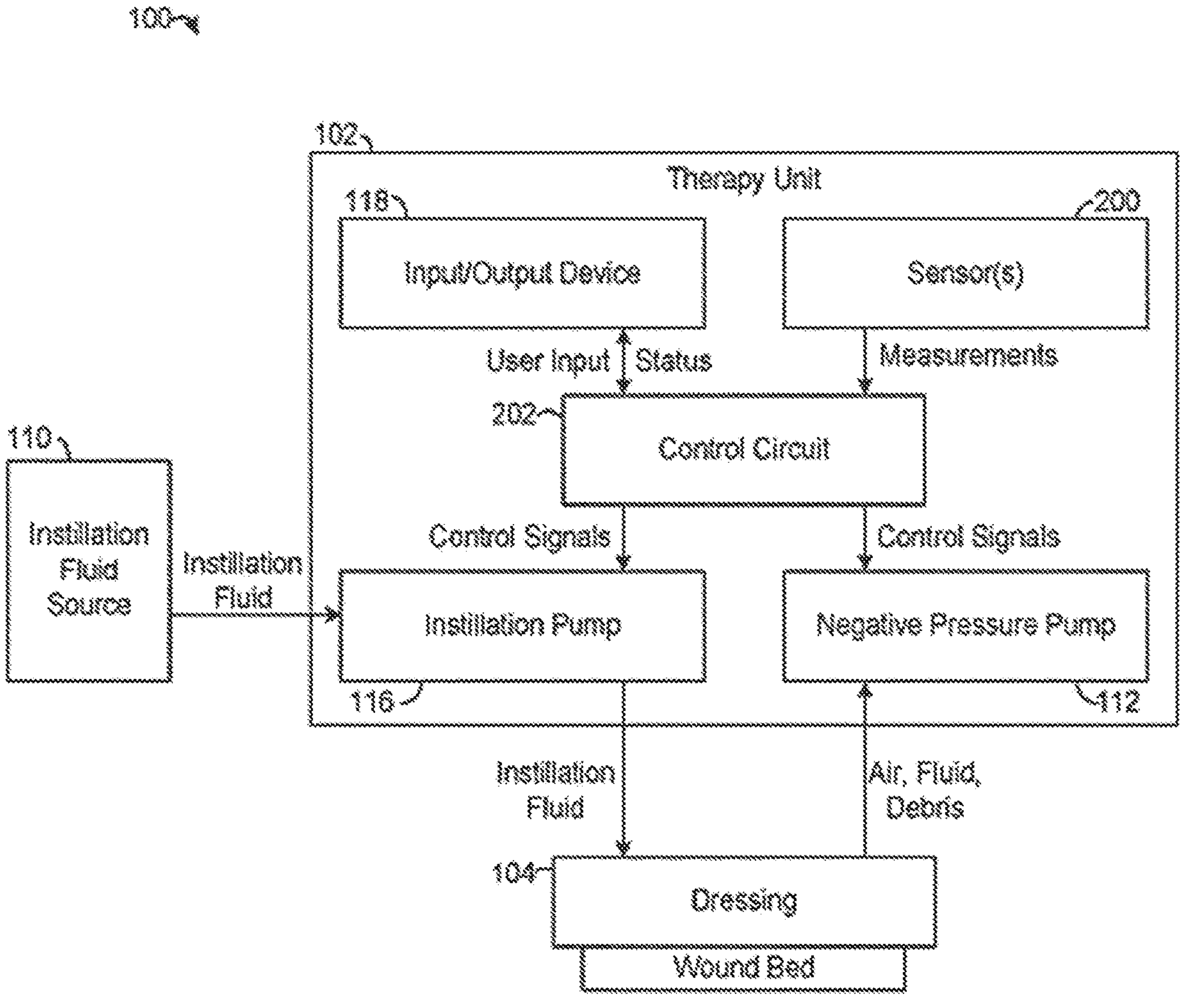
FIG. 8 is a block diagram of the negative pressure and instillation wound therapy system of FIG. 7.
Figure 9:
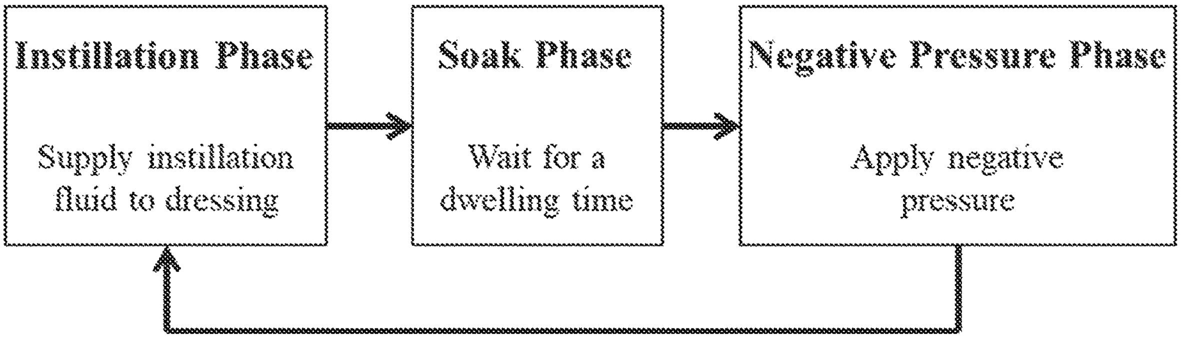
FIG. 9 is a flowchart of a process for negative pressure and instillation wound therapy.

In negative pressure wound therapy with instillation and dwell time, a second tube is introduced (in addition to the one for drainage) for the purpose of intermittently instilling solutions into the wound (e.g., V.A.C. Instill® Wound Therapy, KCI, an Acelity company, San Antonio, TX). Briefly, fluid was instilled via gravity into a foam interface from an intravenous bag or bottle. The solution is held at the wound site for a short period of time (a.k.a., dwell time) followed by removal of wound fluid under negative pressure; this sequence of events was repeated in cycles. FIGS. 7-9 show exemplary negative pressure and instillation wound therapy (NPIWT) system and its functioning.

Referring to FIGS. 7 and 8, exemplary embodiments of a negative pressure and instillation wound therapy (NPIWT) system 100 is shown. FIG. 7 shows a perspective view of the NPIWT system 100, according to an exemplary embodiment. FIG. 8 shows a block diagram of the NPIWT system 100, according to an exemplary embodiment. The NPIWT system 100 may be used to provide instillation therapy by providing instillation fluid to the wound filler composition 104. The NPIWT system 100 is shown to include a therapy unit 102 fluidly coupled to a wound filler composition 104 via a vacuum tube 106 and an instillation tube 108. The NPIWT system 100 is also shown to include an instillation fluid 110, containing a wound instillation fluid composition, fluidly coupled to the instillation tube 108. The NPIWT system 100 is configured to provide negative pressure wound therapy at a wound bed by reducing the pressure at the wound filler composition 104 relative to atmospheric pressure. The NPIWT system 100 may be, for example, a V.A.C. Ulta™ System available from Kinetic Concepts, Inc. (San Antonio, TX).

The wound filler composition 104 is delivered into a wound bed, i.e., a location of a wound (e.g., sore, laceration, burn, etc.) on a patient. The wound filler composition 104 may be substantially sealed over the wound model such that a pressure differential may be maintained between the atmosphere and the wound bed (i.e., across the wound filler composition 104). The wound filler composition 104 may be coupled to the vacuum tube 106 and the instillation tube 108, for example to place the vacuum tube 106 and/or the instillation tube 108 in fluid communication with the wound bed. Any wound filler composition disclosed herein may be implemented in the NPIWT systems disclosed herein.

The therapy unit 102 includes a negative pressure pump 112 (shown in FIG. 8 and obscured within the therapy unit 102 in the perspective view of FIG. 7) configured to pump air, wound exudate, and/or other debris (e.g., necrotic tissue) and/or fluids (e.g., instillation fluid) out of the wound filler composition 104 via the vacuum tube 106, thereby creating a negative pressure at the wound filler composition 104. The negative pressure pump 112 is fluidly communicable with the vacuum tube 106 and the wound filler composition 104. Wound exudate and/or other debris and/or fluids removed from the wound bed by the negative pressure pump 112 may be collected in a canister 114 located on the therapy unit 102.

Operating the negative pressure pump 112 may therefore both create a negative pressure at the wound bed and remove undesirable fluid and debris from the wound bed. In some cases, operating the negative pressure pump 112 may cause deformation of the wound bed and/or provide other energy to the wound bed to facilitate debridement and healing of the wound bed. The negative pressure pump 112 may be operated in accordance with one or more dynamic pressure control approaches that may facilitate wound healing.

The therapy unit 102 also includes an instillation pump 116. The instillation pump 116 is configured to selectively provide instillation fluid from the instillation fluid source 110 to the wound filler composition 104. The instillation pump 116 is operable to control the timing and amount (volume) of instillation fluid provided to the wound filler composition 104. As described in detail below, the instillation pump 116 may be controlled in coordination with the negative pressure pump 112 to provide one or more wound treatment cycles that may facilitate wound healing.

The therapy unit 102 also includes an input/output device 118. The input/output device 118 is configured to provide information relating to the operation of the NPIWT system 100 to a user and to receive user input from the user. The input/output device 118 may allow a user to input various preferences, settings, commands, etc. that may be used in controlling the negative pressure pump 112 and the instillation pump 116 as described in detail below. The input/output device 118 may include a display (e.g., a touch-screen), one or more buttons, one or more speakers, and/or various other devices configured to provide information to a user and/or receive input from a user.

As shown in FIG. 7, the therapy unit 102 may also include one or more sensors 200 and a control circuit 202. The sensor(s) 200 may be configured to monitor one or more of various physical parameters relating to the operation of the NPIWT system 100. For example, the sensor(s) 200 may measure pressure at the vacuum tube 106, which may be substantially equivalent and/or otherwise indicative of the pressure at the wound filler composition 104. As another example, the sensor(s) 200 may measure an amount (e.g., volume) of instillation fluid provided to the wound filler composition 104 by the instillation pump 116. The sensor(s) 200 may provide such measurements to the control circuit 202. The sensor 200 may be coupled or configured to be coupled to the wound filler composition 104 and to the negative-pressure pump 112.

The control circuit 202 is configured to control the operation of the therapy unit 102, including by controlling the negative pressure pump 112, the instillation pump 116, and the input/output device 118. The control circuit 202 may receive measurements from the sensor(s) 200 and/or user input from the input/output device 118 and use the measurements and/or the user input to generate control signals for the instillation pump 116 and/or the negative pressure pump 112. The control circuit 202 may control the negative pressure pump 112 and the instillation pump 116 to provide various combinations of instillation phase, soak phase (corresponding to dwell time), and negative pressure phase to support and encourage wound healing.

Referring to FIG. 9, a flowchart depicting a process for treating a wound using the NPIWT system 100 of FIGS. 7-8 is shown, according to an exemplary embodiment. The NPIWT process is shown as a cycle through three phases, namely an instillation phase, a soak phase, and a negative pressure phase. The control circuit 202 may be configured to control the instillation pump 116 and the negative pressure pump 112 to execute the process.

At the instillation phase, the control circuit 202 controls the instillation pump 116 to provide instillation fluid from the instillation fluid source 110 to the wound filler composition 104 via the instillation tube 108. In one illustrative embodiment, the instillation fluid source 110 may include a storage component for the solution and a separate cassette for holding the storage component and delivering the solution to a tissue site, such as a V.A.C. VeraLink™ Cassette available from Kinetic Concepts, Inc. (San Antonio, TX). At the instillation phase, the control circuit 202 may control the instillation pump 116 to provide a particular amount (e.g., volume) of instillation fluid and/or to provide instillation fluid for a particular duration of time. Instillation fluid may thereby be placed in contact with the wound bed. The amount of instillation fluid provided at the instillation phase and/or the duration of time of the instillation phase may be user-selectable (e.g., by a doctor, nurse, caregiver, patient) via the input/output device 118 and/or otherwise customizable (e.g., for various wound types, for various types of instillation fluid).

At the soak phase, the control circuit 202 provides a dwelling time between the instillation phase and the negative pressure phase. During the soak phase, the control circuit 202 controls the instillation pump 116 to prevent additional fluid from being added to the wound filler composition 104 and prevents the negative pressure pump 112 from operating. The soak phase thereby provides a dwelling time during which the instillation fluid added at the instillation phase can soak into the wound model, for example to soften, loosen, dissolve, etc. the biofilm. The duration of the soak period may be user-selectable via the input/output device 118 and/or otherwise customizable (e.g., for various wound types, for various types of instillation fluid). For example, the soak period may have a duration of between ten seconds and 20 minutes.

At the negative pressure phase, the control circuit 202 controls the negative pressure pump 112 to create a negative pressure at the wound filler composition 104. In some embodiments, the instillation pump 116 is also controlled to provide instillation fluid to the wound filler composition 104 during the negative pressure phase.

During the negative pressure phase, the negative pressure pump 112 is controlled to remove air, tryptic soy broth medium, biofilm and/or debris from the wound bed and the wound filler composition 104. In some cases, the negative pressure pump 112 may remove the instillation fluid 110 added at the instillation phase. The instillation phase, the soak phase, and the negative pressure phase thereby work together to provide improved wound therapy.

As illustrated by FIG. 9, the control circuit 202 may control the NPIWT system 100 to repeatedly cycle through the sequence of the instillation phase, the soak phase, and the negative pressure phase. Various parameters (e.g., amount of instillation fluid 110 provide, the length of the soak phase, the low pressure value, the high pressure value) of the phases may remain constant between cycles, may vary between cycles, or some combination thereof. Accordingly, the NPIWT process is highly configurable for various wound types, wound sizes, patients, instillation fluids, etc.

Other NPIWT systems are described in US Publication Nos. 20170182230, and 20180214315, the contents of which are herein incorporated by reference in their entirety.

Therapeutic Methods Including the Wound Filler Compositions of the Present Technology In one aspect, the present disclosure provides a method for treating a wound in a subject in need thereof, wherein the method comprises administering to the wound a wound filler composition of any embodiment disclosed herein. Additionally or alternatively, in some embodiments of the methods disclosed herein, the wound may be an acute wound, a deep wound, a partial thickness wound, or a chronic wound. Additionally or alternatively, in some embodiments of the methods disclosed herein, the wound is an acute wound selected from the group consisting of burns, skin grafts, and dehisced surgical wounds. Additionally or alternatively, in some embodiments of the methods disclosed herein, the wound is a chronic wound selected from the group consisting of infectious wounds, venous ulcers, arterial ulcers, decubitis ulcers and diabetic ulcers.

In another aspect, the present disclosure provides a method for treating a wound in a subject in need thereof, wherein the method includes (a) administering the wound filler composition of the present technology to a wound, wherein the wound filler composition is configured to fill an entire volume of the wound; (b) providing a device to the wound, wherein the device comprises: a drape, optionally a retainer layer, and a vacuum source for applying negative pressure to the wound, wherein the vacuum source is configured to be fluidly connected to the drape through tubing; (c) optionally applying the retainer layer over the wound filler composition; (d) applying the drape over the wound filler composition and/or the retainer layer, wherein the drape is configured to seal the wound filler composition and/or the retainer layer and the wound; and (e) applying negative pressure to the wound.

The wound filler composition of the present technology may be used in conjunction with the automated systems and methods described herein including, for example, administering the wound filler composition into a wound cavity, instilling a wound instillation fluid composition in a continuous or intermittent mode followed by negative pressure therapy for treating the wound at the tissue site.

In one aspect, the present disclosure provides a method for treating a wound in a subject in need thereof, comprising (a) administering any and all embodiments of the wound filler compositions disclosed herein to a wound, wherein the wound filler composition is configured to fill an entire volume of the wound; (b) providing a device to the wound, wherein the device comprises: a drape, optionally a retainer layer, an instillation pump configured to instill a wound instillation fluid composition to the wound filler composition, and a vacuum source for applying negative pressure to the wound, wherein each of the vacuum source and the instillation pump are fluidly connected to the drape through tubing; (c) optionally applying the retainer layer over the wound filler composition; (d) applying the drape over the wound filler composition and/or the retainer layer, wherein the drape is configured to seal the wound filler composition and/or the retainer layer and the wound; (e) instilling the wound instillation fluid composition to the wound filler composition; (f) soaking the wound in the wound instillation fluid composition for a first temporal interval; (g) applying negative pressure on the wound for a second temporal interval; and (h) repeating steps (e)-(g) at least once.

Additionally or alternatively, in some embodiments of the methods of the present technology, steps (e)-(g) are repeated for about 2 to about 1000 cycles. In certain embodiments of the methods disclosed herein, steps (e)-(g) are repeated for about 2 to about 6 cycles, about 5 to about 15 cycles, about 10 to about 30 cycles, about 20 to about 60 cycles, about 50 to about 150 cycles, about 100 to about 300 cycles, about 200 to about 600 cycles, about 300 to about 1000 cycles, or any range including and/or in between any two of these values.

In one aspect, the present disclosure provides a method for treating (a) administering any and all embodiments of the wound filler composition disclosed herein to a wound, wherein the wound filler composition is configured to fill an entire volume of the wound; (b) providing an instillation pump configured to instill a wound instillation fluid composition to the wound filler composition, and a vacuum source for applying negative pressure to the wound, wherein the vacuum source is fluidly connected to the wound filler composition through a first tube connection and the instillation pump is fluidly connected to the wound filler composition through a second tube connection; (c) instilling the wound instillation fluid composition to the wound filler composition; (d) soaking the wound in the wound instillation fluid composition for a first temporal interval; (e) applying negative pressure on the wound for a second temporal interval; and (f) repeating steps (c)-(e) at least once. In some embodiments of the methods disclosed herein, steps (c)-(e) are repeated for about 2 to about 1000 cycles. In certain embodiments of the methods disclosed herein, steps (c)-(e) are repeated for about 2 to about 6 cycles, about 5 to about 15 cycles, about 10 to about 30 cycles, about 20 to about 60 cycles, about 50 to about 150 cycles, about 100 to about 300 cycles, about 200 to about 600 cycles, about 300 to about 1000 cycles, or any range including and/or in between any two of these values.

In any embodiment disclosed herein, the wound filler composition may be configured to be adjoined to a retainer layer while in use for NPWT. The retainer layer may include, but is not limited to, a cellular foam, an open-cell foam, a reticulated foam, porous tissue collections, and/or other porous material (e.g., gauze). The retainer layer may have pores that range in diameter from about 60 μm to about 2000 μm. Thus, the retainer layer may have pores that range in diameter from about 60 μm, about 100 μm, about 250 μm, about 500 μm, about 750 μm, about 1000 μm, about 1250 μm, about 1500 μm, about 1750 μm, about 2000 μm, or any range including and/or in between any two of these values. In some embodiments, the retainer layer may include an open-cell, reticulated polyurethane foam such as a GRANUFOAM™ dressing available from Kinetic Concepts, Inc. of San Antonio, Texas. In some embodiments, the retainer layer may include an open-cell, reticulated polyurethane foam such as a V.A.C. VERAFLO™ dressing available from Kinetic Concepts, Inc. of San Antonio, Texas or a V.A.C. VERAFLO CLEANSE CHOICE™ dressing (Acelity, San Antonio TX).

In any embodiment disclosed herein, the drape may be composed of a polyurethane film or an elastomeric film. The drape may be applied over the wound filler composition of the present technology and/or the retainer layer during NPWT. The drape may be configured to seal the wound filler composition and/or the retainer layer, and the wound site during NPWT. Examples of an elastomeric film include, but are not limited to, natural rubber, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, ethylene vinyl acetate (EVA) film, copolyester, or silicone. Suitable drape materials and methods of use are described in U.S. Pat. Nos. 7,534,240, 7,611,500, 9,918,733, and 10,143,485, of which the entire contents are incorporated herein by reference.

In any embodiment disclosed herein, the wound filler composition may be connected to tubing while in use for NPWT. The tubing may include, but is not limited to, a tube, pipe, hose, conduit, or any other structure with one or more lumina adapted to convey liquid between two ends. Additionally or alternatively, in some embodiments, the tubing may be composed of polyvinyl chloride, polyethylene, polypropylene, or any combination thereof. The tubing or tube connections may be configured to connect the drape to an instillation pump or a vacuum source for applying negative pressure, such as a V.A.C.® Therapy system, while in use for NPWT. Suitable tubing materials and methods of use are described in U.S. Pat. Nos. 7,534,240, 7,611,500, 9,918,733, and 10,143,485, of which the entire contents are incorporated herein by reference.

In any embodiment disclosed herein, the wound filler composition may be fluidly coupled to a vacuum via the tubing to apply negative pressure to a wound in need thereof. Additionally or alternatively, in some embodiments, negative pressure refers to a pressure less than local ambient pressure, such as the pressure in a local environment external to a sealed wound site. Additionally or alternatively, in some embodiments, the vacuum for applying negative pressure may be a vacuum pump, a suction pump, a micro-pump, or a wall vacuum port available in many healthcare facilities. Additionally or alternatively, in some embodiments, the vacuum is used to apply negative pressure to a wound. Additionally or alternatively, in some embodiments, the negative pressure applied to a wound may be about −5 mm Hg to about −500 mm Hg, or about −75 mm Hg to about −300 mm Hg. Thus, the negative pressure applied to a wound may be about −5 mm Hg, about −25 mm Hg, about −50 mm Hg, about −75 mm Hg, about −100 mm Hg, about −125 mm Hg, about −150 mm Hg, about −175 mm Hg, about −200 mm Hg, about −225 mm Hg, about −250 mm Hg, about −275 mm Hg, about −300 mm Hg, about −325 mm Hg, about −350 mm Hg, about −375 mm Hg, about −400 mm Hg, about −425 mm Hg, about −450 mm Hg, about −475 mm Hg, about −500 mm Hg, or any range including and/or in between any two of these values. Methods of use of negative pressure therapy devices are described in U.S. Pat. Nos. 7,534,240, 7,611,500, 9,918,733, and 10,143,485, of which the entire contents are incorporated herein by reference.

Additionally or alternatively, in some embodiments of the methods disclosed herein, negative pressure may be applied to the wound for about 1 second to about 100 minutes. Accordingly, in some embodiments, the second temporal interval is about 1 second, about 5 seconds, about 10 seconds, about 15 seconds, about 30 seconds, about 45 seconds, about 1 minute, about 1.25 minutes, about 2 minutes, about 4 minutes, about 6 minutes, about 8 minutes, about 10 minutes, about 12 minutes, about 14 minutes, about 16 minutes, about 18 minutes, about 20 minutes, about 25 minutes, about 30 minutes, about 35 minutes, about 40 minutes, about 45 minutes, about 50 minutes, about 60 minutes, about 70 minutes, about 80 minutes, about 90 minutes, about 100 minutes, or any range including and/or in between any two of these values.

Additionally or alternatively, in some embodiments of the methods disclosed herein, about 1 ml to about 20 ml of a wound instillation fluid composition may be instilled per cycle. Additionally or alternatively, in some embodiments, about 1 ml, about 2 ml, about 4 ml, about 6 ml, about 8 ml, about 10 ml, about 12 ml, about 14 ml, about 16 ml, about 20 ml, or any range including and/or in between any two of these values of any and all embodiments of the wound instillation fluid composition may be instilled per cycle. In some embodiments, the wound instillation fluid composition comprises saline solution.

Additionally or alternatively, in some embodiments of the methods disclosed herein, the first temporal interval (dwell time) may be about 1 second to about 30 minutes. Additionally or alternatively, in some embodiments, the first temporal interval (dwell time) may be about 1 second, about 5 seconds, about 10 seconds, about 15 seconds, about 30 seconds, about 45 seconds, about 1 minute, about 1.25 minutes, about 1.5 minutes, about 1.75 minutes, about 2 minutes, about 2.25 minutes, about 2.5 minutes, about 2.75 minutes, about 3 minutes, about 3.5 minutes, about 4 minutes, about 5 minutes, about 6 minutes, about 8 minutes, about 10 minutes, about 12 minutes, about 15 minutes, about 18 minutes, about 20 minutes, about 25 minutes, about 30 minutes, or any range including and/or in between any two of these values.

Additionally or alternatively, in some embodiments of the methods of the present technology, steps (e)-(g) are repeated for about 2 to about 1000 cycles. In certain embodiments of the methods disclosed herein, steps (e)-(g) are repeated for about 2 to about 6 cycles, about 5 to about 15 cycles, about 10 to about 30 cycles, about 20 to about 60 cycles, about 50 to about 150 cycles, about 100 to about 300 cycles, about 200 to about 600 cycles, about 300 to about 1000 cycles, or any range including and/or in between any two of these values.

Any method known to those in the art for administering the wound filler composition to an acute wound or a chronic wound disclosed herein may be employed. Suitable methods include in vitro or in vivo methods. In vivo methods typically include the administration of one or more wound filler compositions to a subject in need thereof, suitably a human. In any embodiment disclosed herein, the wound filler composition may be applied directly to the wound. In any embodiment disclosed herein, the wound filler composition may be applied directly to a wound. When used in vivo for therapy, the wound filler composition described herein are administered to the subject in effective amounts (i.e., amounts that have desired therapeutic effect). Additionally or alternatively, in some embodiments, the subject is human.

Additionally or alternatively, in some embodiments, the wound filler compositions may be administered weekly, bi-weekly, tri-weekly, or monthly. Additionally or alternatively, in some embodiments, the wound filler compositions may be administered for a period of one, two, three, four, or five weeks. Additionally or alternatively, in some embodiments, the wound filler compositions may be administered for six weeks or more. Additionally or alternatively, in some embodiments, the wound filler compositions may be administered for twelve weeks or more. Additionally or alternatively, in some embodiments, the wound filler compositions may be administered for a period of less than one year. Additionally or alternatively, in some embodiments, the wound filler compositions may be administered for a period of more than one year.

EXAMPLES

The present technology is further illustrated by the following Examples, which should not be construed as limiting in any way.

Figure 2:
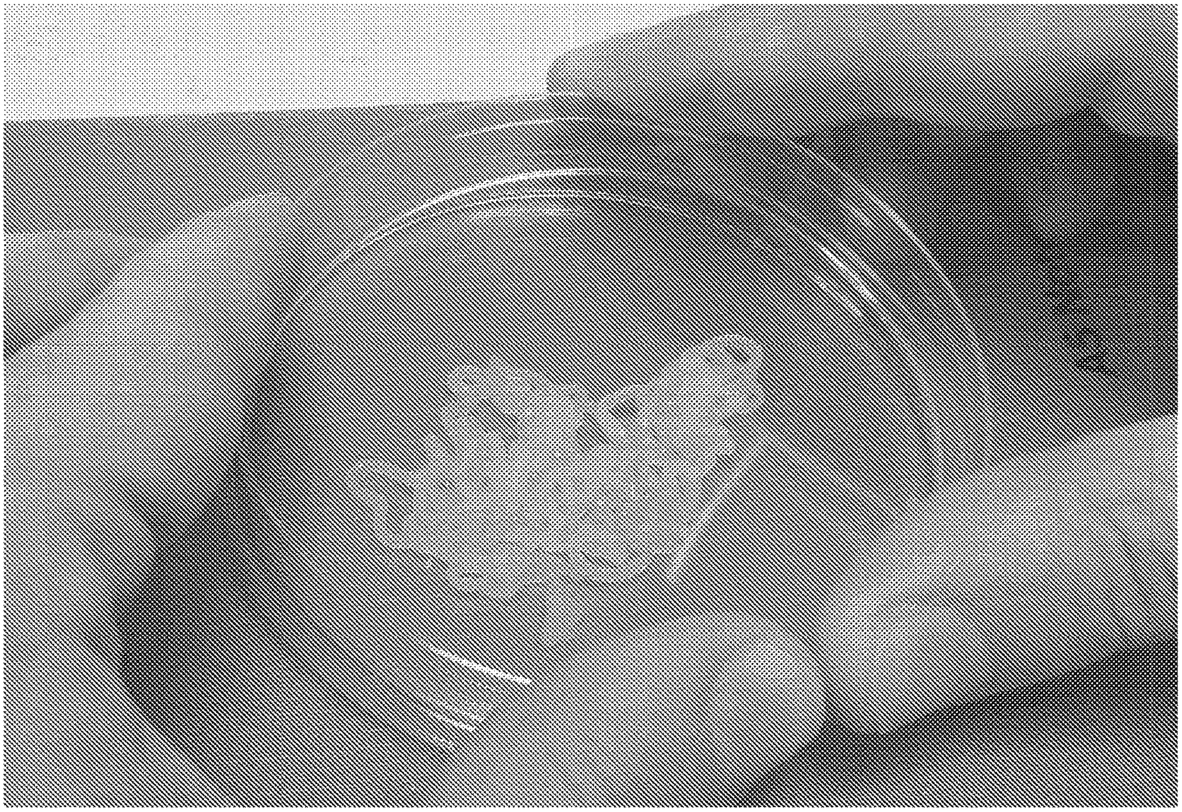
FIG. 2 shows a representative image of a calcium alginate string when compressed. The calcium alginate string exhibited good resistance to compression indicating a high potential to manifold fluid and pressure in a wound under NPWT.

Example 1: Low Viscosity Forms of Calcium Alginate Filler with Higher Solids Content Withstand Compressive Forces Due to Negative Pressure A deployable wound filler composition comprising calcium alginate strings was prepared by mixing sodium alginate in the form of an aqueous paste with a calcium salt such as 1-10% $CaCl_2$ in a mixer nozzle. The calcium alginate extrusions were dispensed from an aerosol type dispenser such as a compressed gas canister. Without wishing to be bound by theory, it is believed that ion exchange occurs rapidly such that the water insoluble and cross-linking calcium alginate is formed as it emerges from the nozzle of the aerosol canister. See FIG. 1. These calcium alginate strings had a durometer equivalent of about 60 shore and showed robust resistance to compression demonstrating that the deployable calcium alginate wound filler has a high potential to manifold fluid and pressure in a wound under negative pressure wound therapy (NPWT). See FIG. 2.

Figure 3A:
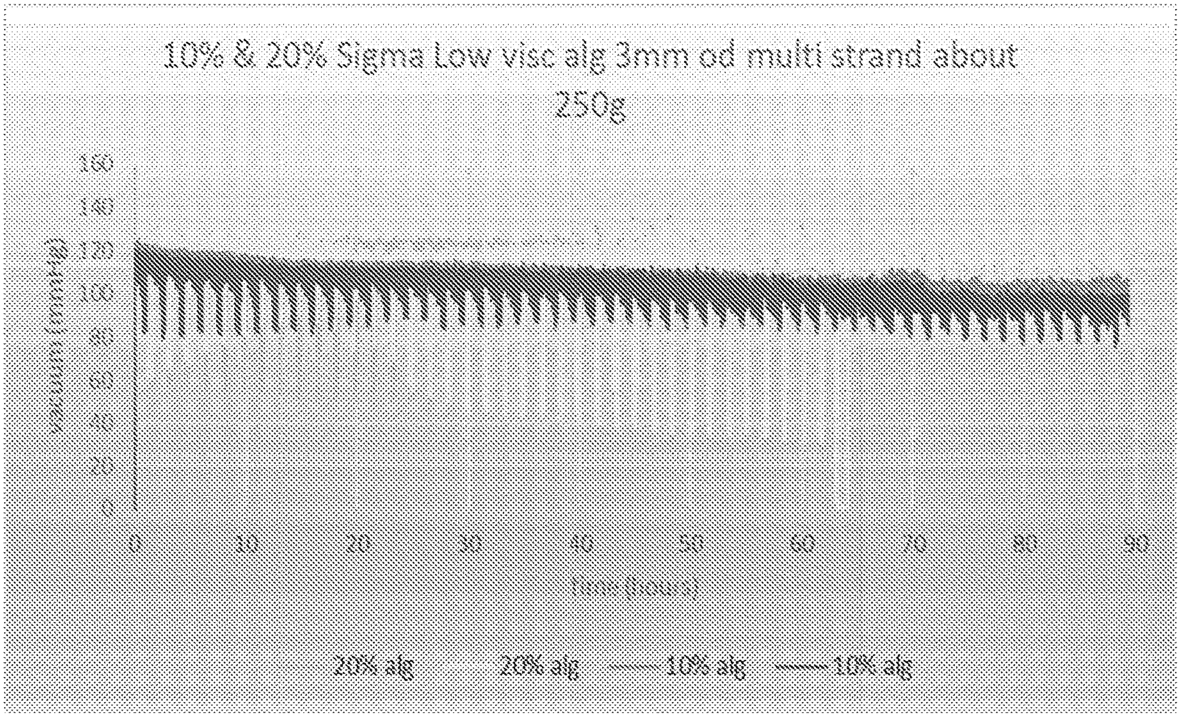
FIG. 3A shows a graph illustrating the mechanical strength of the calcium alginate produced using the methods of the present technology. In particular, calcium alginate produced with higher solid content low viscosity forms of sodium alginate withstood compressive forces due to negative pressure and manifold consistency for over 65 hours. The calcium alginate was produced with 10% or 20% low viscosity sodium alginate obtained from Sigma-Aldrich. The calcium alginate string tested had an outer diameter of 3 mm and weighed 250 g. Measurements were taken at two different locations of a wound model.
Figure 3B:
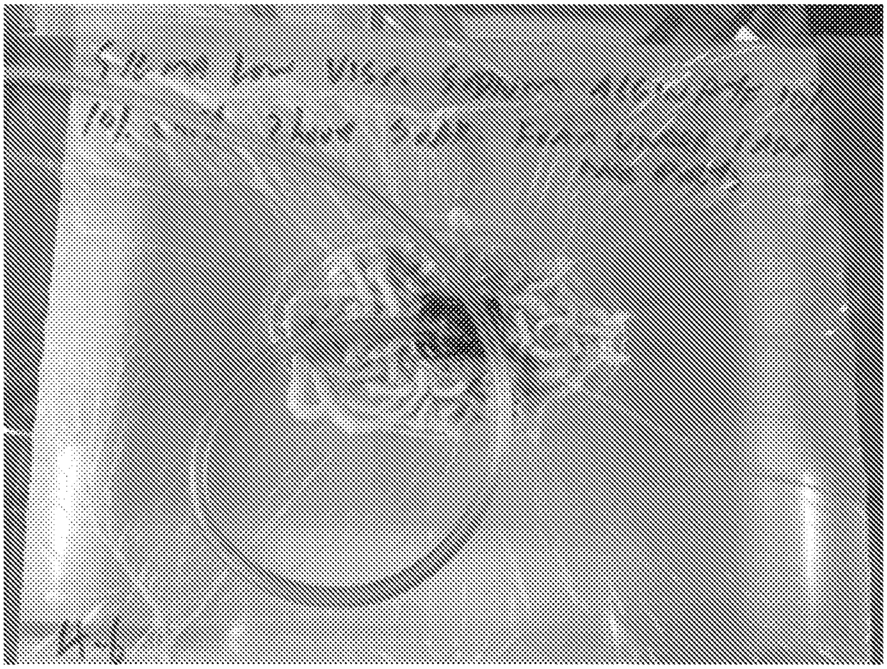
FIG. 3B shows a photograph illustrating the measurement of the mechanical strength of the 10% weight/weight low viscosity calcium alginate string of the present disclosure and its ability to withstand negative pressure. The calcium alginate strings were placed in a 30 mm deep flexible wound model, and covered with foam before pressure was applied. The foam was placed under the track pads of the NPWT device. The calcium alginate strings had a 2 mm outer diameter, weighed 250 g, and was made with Sigma-Aldrich 10% weight/weight low viscosity sodium alginate soaked with 10% Calcium Chloride ($CaCl_2$) for two hours.
Figure 3C:
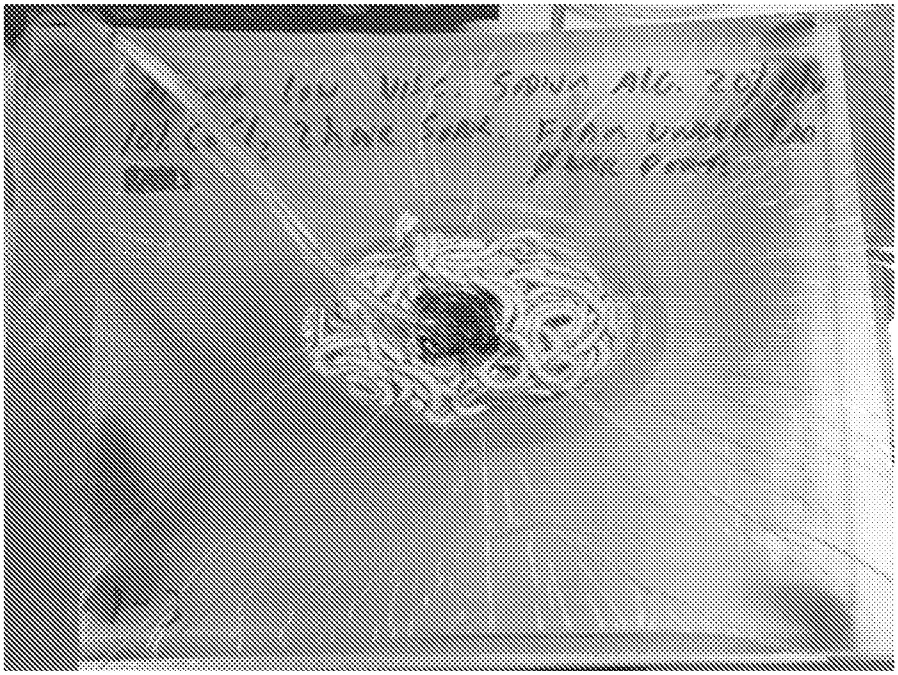
FIG. 3C shows a photograph illustrating the measurement of the mechanical strength of the 20% weight/weight low viscosity calcium alginate string of the present disclosure and its ability to withstand negative pressure. The calcium alginate strings had a 2 mm outer diameter, weighed 250 g, and was made with Sigma-Aldrich 20% weight/weight low viscosity sodium alginate soaked with 10% Calcium Chloride ($CaCl_2$) for two hours.

The sodium or potassium alginate may be low or high viscosity forms. In some embodiments, the low viscosity form of sodium or potassium alginate may have a solids content of up to 10%-25% w/w. FIG. 3A-3C show data from a manifold test and was designed to show how well pressure is distributed through a wound filler. A pressure of −125 mmHg was applied to the wound via a TRAC pad placed on the top of the wound filler (alginate) as shown in FIG. 3B, and any pressure transmitted through the filler was measured at the ports at the base of the wound (2 ports per wound, one at each extremity). The yellow and orange traces were virtually identical (excluding the downward spikes which were the result of a purge cycle from the therapy device) and remained very close to the applied pressure for the duration of the test. Whereas the blue and purple traces fall away from the applied pressure with time indicating that there was a pressure drop as a result of the alginate wound filler collapsing and reducing the available pathways that are required to give good pressure distribution. As shown in FIG. 3A-3C, the low viscosity forms with higher solid content (e.g., 20% w/w) may be more able to withstand the compressive forces due to negative pressure and maintain manifolding consistency.

Figure 4A:
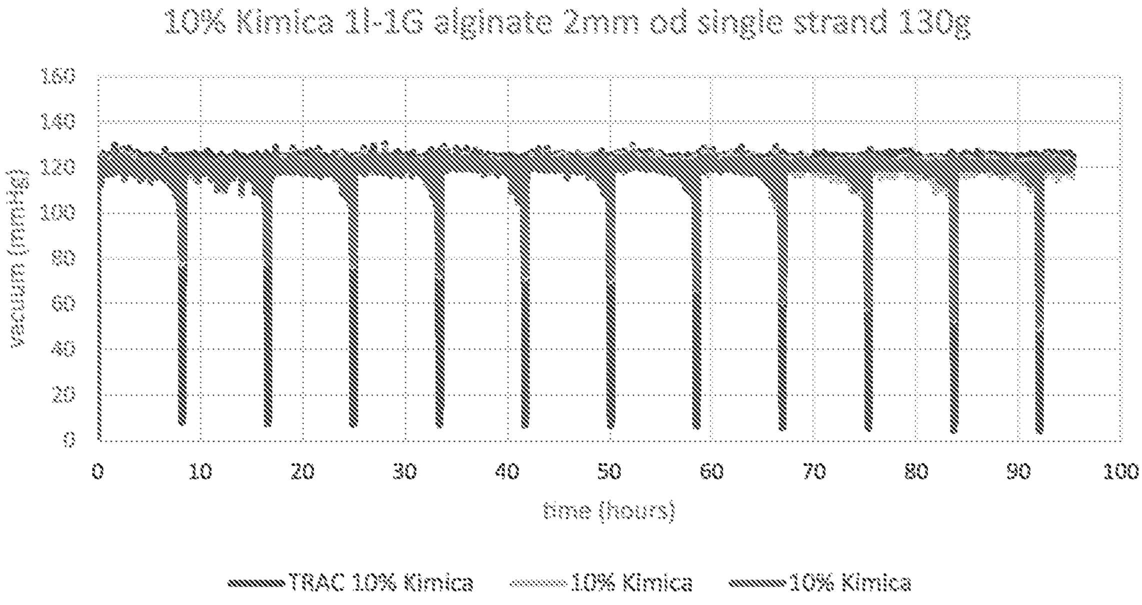
FIG. 4A shows a graph illustrating the mechanical strength of a high guluronate (high "G") calcium alginate filler of the present disclosure produced using high "G" 10% Kimica 11-1G sodium alginate from Kimica Corporation. In particular, calcium alginate produced with high "G" low viscosity sodium alginate withstood compressive forces due to negative pressure and manifold consistency for over 65 hours. The calcium alginate string tested had an outer diameter of 2 mm and weighed 130 g. Measurements were taken at two different locations of a wound model. TRAC refers to the applied pressure (−125 mmHg). The downward spike should be disregarded as these correspond to therapy unit purge sequence.
Figure 4B:
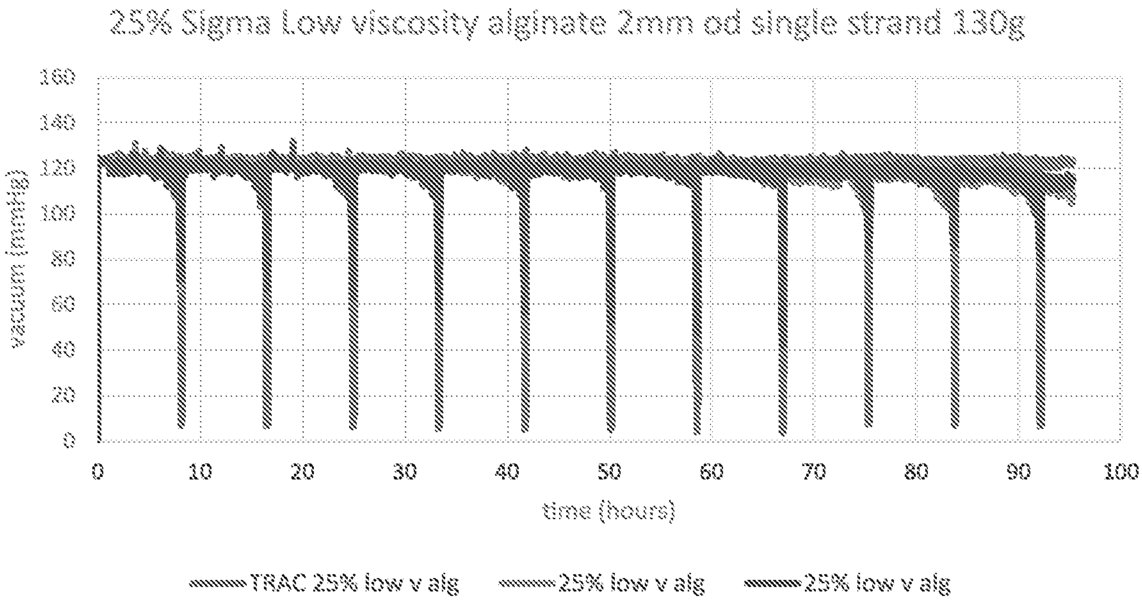
FIG. 4B shows a graph illustrating the mechanical strength of a high strength calcium alginate filler of the present disclosure produced using Sigma-Aldrich 25% low viscosity sodium alginate. The calcium alginate string tested had an outer diameter of 2 mm and weighed 130 g. Measurements were taken at two different locations of a wound model. TRAC refers to the applied pressure (−125 mmHg).
Figure 4C:
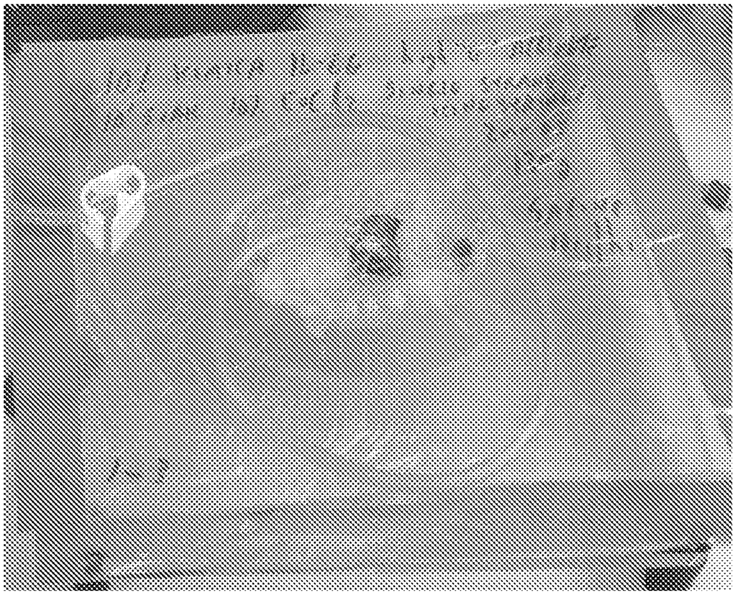
FIG. 4C shows a photograph illustrating the measurement of the mechanical strength of the calcium alginate filler of FIG. 4A. Single strand calcium alginate string was injected into a 14 mm wound model with a syringe, covered with foam before pressure was applied. The calcium alginate string had a 2 mm outer diameter, weighed 130 g, and was made with 10% Kimica Corporation IL-GG high "G" sodium alginate soaked with 10% Calcium Chloride ($CaCl_2$) for 10 minutes. The wound was perfused with saline at 10 cc/hr.
Figure 4D:
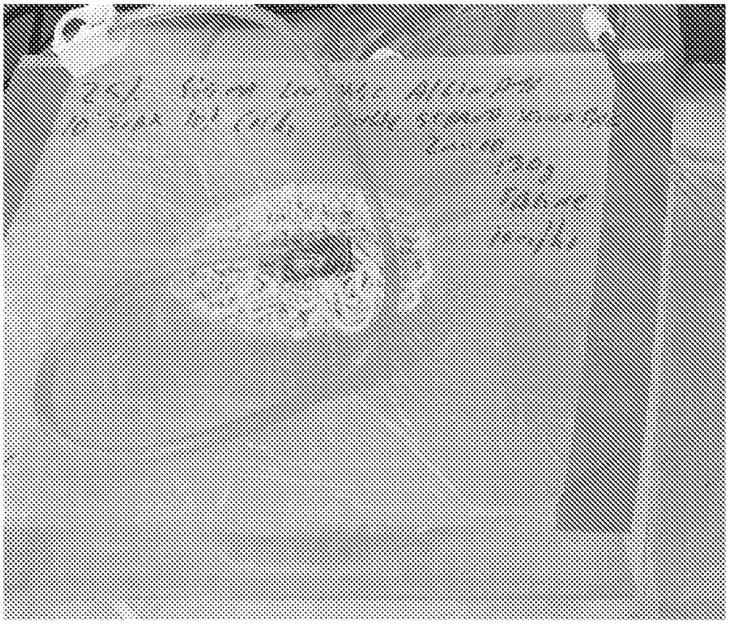
FIG. 4D shows a photograph illustrating the measurement of the mechanical strength of the calcium alginate filler of FIG. 4B. Single strand calcium alginate string was injected into a 14 mm wound model with a syringe, and was covered with foam before pressure was applied. The calcium alginate string had a 2 mm outer diameter, weighed 130 g, and was made with Sigma-Aldrich 25% low viscosity sodium alginate soaked with 10% Calcium Chloride ($CaCl_2$) for 10 minutes. The wound was perfused with saline at 10 cc/hr.

Furthermore, to increase the strength of the alginate filler the alginate may comprise a high guluronate [G] fraction (high "G"). Alginates are commonly copolymers of guluronate and mannuronate [M] forms, where the former gives strength. High guluronate [G] alginate are known in the art and may be supplied by Kimica Corporation, Japan). FIGS. 4A and 4C: The green and yellow traces were very close to the applied pressure (red trace) indicating little or no deterioration in manifolding (pressure transmission through the wound filler). When compared to the 10% solids trace (FIG. 3A) there was a significant improvement in pressure transmission, indicating that the higher guluronic form is better able to withstand the application of negative pressure—this is probably related to the higher mechanical strength shown by the high guluronic acid form compared to the high mannuronic form. FIGS. 4B and 4D: This may be seen as a similar trace to FIG. 3A—same alginate with slightly higher solids content and smaller outer diameter (OD) strand. There was just a little more of a pressure drop towards the end of the test which apart from test-to-test variation, which may be due to the higher wound packing of the wound (smaller OD strands will pack 'tighter together than larger OD strands) leading to a slightly higher pressure drop (poorer manifolding).

As shown in FIGS. 4A-4D, high "G" alginate are able to withstand pressure as well as low viscosity alginate having a solids content of 25% w/w produced by Sigma-Aldrich. FIG. 4A illustrates improved manifolding with a higher guluronic acid alginate with the same strand od and same filler mass (130 g) compared to FIG. 3A.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A canister comprising a first compartment, a second compartment, and a gas cartridge comprising a pressuring gas, wherein the first compartment includes sodium alginate or potassium alginate and the second compartment includes a multivalent cation salt, and wherein the canister is configured to dispense a multivalent cation alginate string having a durometer equivalent to about 20-70 shore and a diameter of 1-4 mm.

2. The canister of claim 1, wherein the sodium alginate or potassium alginate is in the form of an aqueous paste or dry powder.

3. The canister of claim 1, wherein the pressuring gas is carbon dioxide ($CO_2$).

4. The canister of claim 1, further comprising a mixer nozzle that is configured to (a) receive the sodium alginate or potassium alginate from the first compartment and the multivalent cation salt from the second compartment and (b) mix the sodium alginate or potassium alginate with the multivalent cation salt to form an alginate mixture.

5. The canister of claim 1, wherein the multivalent cation alginate string includes an inner layer of sodium or potassium alginate and an outer layer of the multivalent cation salt.

6. The canister of claim 1, wherein the multivalent cation alginate string includes an outer layer of sodium or potassium alginate and an inner layer of the multivalent cation salt.

* * * * *